United States Patent [19]

Edwards et al.

[11] Patent Number: 5,089,451

[45] Date of Patent: Feb. 18, 1992

[54] HARDENED CATALYST PARTICLES AND METHOD FOR HARDENING THE CATALYST PARTICLES

[75] Inventors: James H. Edwards; Ashit M. Maitra; Ralph J. Tyler, all of New South Wales, Australia

[73] Assignees: The Broken Hill Proprietary Company, Ltd., Melbourne; Commonwealth Scientific and Industrial Research Organization, Campbell, both of Australia

[21] Appl. No.: 545,957

[22] Filed: Jul. 2, 1990

[30] Foreign Application Priority Data

Jun. 30, 1989 [AU] Australia ............................. PJ5021
Aug. 16, 1989 [AU] Australia ............................. PJ5806

[51] Int. Cl.$^5$ ...................... B01J 27/232; B01J 23/02; B01J 23/04
[52] U.S. Cl. ...................................................... 502/174
[58] Field of Search ............... 502/174, 34; 423/419, 423/421, 430

[56] References Cited

U.S. PATENT DOCUMENTS

| 2,587,599 | 3/1952 | Corson et al. | 502/174 |
| 3,758,673 | 9/1973 | Buben et al. | 502/174 X |
| 3,974,098 | 8/1976 | Gavin | 502/174 |

OTHER PUBLICATIONS

Reisman, "Reactions of the Group VB Pentoxides with Alkali Oxides and Carbonates. IX. A DTA Study of Alkali Metal Carbonates", *J.A.C.S.*, 1958, 80, 3358.

*Primary Examiner*—W. J. Shine
*Attorney, Agent, or Firm*—Armstrong, Nikaido, Marmelstein, Kubovcik & Murray

[57] ABSTRACT

Catalysts containing a carbonate or carbonates, particularly Group IA and IIA carbonates, may be hardened sufficiently to be useable in fluidized bed reactors. The catalysts are heated to at least 700° C. in an atmosphere containing carbon dioxide under a partial pressure above the dissociation pressure of the carbonate form of the catalyst.

8 Claims, No Drawings

HARDENED CATALYST PARTICLES AND METHOD FOR HARDENING THE CATALYST PARTICLES

FIELD OF THE INVENTION

The present invention relates to a method for the hardening of catalysts particularly, though not exclusively, to enable particles of those catalysts to be used in fluidised bed reactors. The invention also relates to the catalysts produced by the method according to the present invention.

BACKGROUND ART

It is known that the oxides and carbonates of a number of elements, and particularly Group IIA elements, have catalytic properties. The catalytic properties are particularly useful for the oxidative coupling of methane to form higher hydrocarbons. These oxides and carbonates may be used as fixed bed catalysts or as fluidised bed catalysts. In the former case a stream of gas containing the reactant molecules is caused to flow past a stationary bed of catalyst particles. In the latter case the particles are constantly mobile within an upflowing stream of the reactant gas. This movement causes abrasion and spalling of the catalyst particles. The resulting dust can then be carried out of the fluidised bed reactor in the gas stream.

For many large scale operations fluidised bed reactors are preferred, however carbonate catalysts, and particularly Group IIA carbonate catalysts, are relatively soft and are therefore not suitable for use in fluidised bed reactors.

DISCLOSURE OF THE INVENTION

It has now been discovered that particles of carbonate catalysts can be hardened by firing in an atmosphere containing carbon dioxide.

The present invention consists in a method for hardening a catalyst containing a compound that is capable, under the hardening conditions, of existing at least partly in the form of a carbonate, comprising heating the catalyst to a temperature of at least 700° C. in an atmosphere containing carbon dioxide, preferably under a partial pressure of carbon dioxide above the dissociation pressure of the carbonate form of the catalyst compound, so as to retain that compound at least partly in the carbonate form.

In a further aspect the present invention relates to a hardened catalyst produced by the method according to the present invention.

The present invention is particularly applicable to catalysts which are, or in part comprise, carbonates of Group IA and/or group IIA elements. It can, however, be applied with advantage to other carbonate compounds. These carbonates and their corresponding oxides are known to have catalytic properties; however, the carbonates are relatively soft which reduces their practical applications as catalysts particularly in fluidised bed applications. If these carbonates are sintered in a conventional manner i.e. by heating in air, the relatively low stability carbonates are rapidly converted to the much more refractory oxides. This necessitates heating the catalysts to temperatures substantially above 1000° C. to achieve any worthwhile sintering and thus hardening of the catalyst.

By heating the catalyst in an atmosphere of carbon dioxide, preferably at a partial pressure which exceeds the dissociation pressure of the carbonate, the dissociation of the carbonate into a corresponding oxide is retarded. Sintering of the carbonate takes place at a substantially lower temperature than would otherwise be possible.

The catalyst is preferably heated to a temperature approaching, but below, the melting point of the carbonate compound. The heating period should be sufficient to induce hardening. This heating period is preferably at least one hour and more preferably at least three hours. It will be appreciated that the required period of heating is related to the temperature to which the catalyst is raised and the carbon dioxide concentration in the atmosphere. Simple routine experimentation will reveal the best combination of temperature and heating period for any given carbonate containing catalyst.

BEST METHOD OF CARRYING OUT THE INVENTION

The following examples exemplify the best method of carrying out the invention.

EXAMPLE 1

An embodiment of the catalyst hardening process according to the present invention is described below.

Samples of a strontium carbonate and bentonite catalyst were heated at 1000° C. for 4 hours in (a) an inert gas, nitrogen ($N_2$) and (b) carbon dioxide ($CO_2$) atmospheres. The hardening process was accompanied by considerable shrinkage in the size of the individual particles and this resulted in a reduction in their surface areas. Surface area measurements by a conventional B.E.T. technique were made on the fresh untreated catalyst and those heated in $N_2$ and $CO_2$ atmospheres. The results are given in the accompanying table.

| Sample | Surface Area $m^2/g$ |
| --- | --- |
| Fresh untreated | 15.0 |
| Heated in $N_2$ (4 hours 1000° C.) | 7.1 |
| Heated in $CO_2$ (4 hours 1000° C.) | 0.3 |

Catalysts hardened in an atmosphere of $CO_2$ have been successfully used in fluidised-bed reactors for many hours with no measurable weight loss due to attrition and dust formation.

EXAMPLES 2-4

A hardness index for catalysts was derived from a simple agitation test that allowed adequate discrimination between samples. Equal weights of catalysts sized $-250+150$ um and of 2 mm glass beads were mechanically shaken for 10 mins. The sample was then reclassified and weight of particles remaining with a size of $-250+150$ um determined. The hardness index equates to the percentage of the catalyst that retained its original size. The improvement in hardness index for catalyst based on Group IIA elements after firing in $CO_2$ is demonstrated in the following samples.

A $SrCO_3$ catalyst was prepared by slurrying $SrCO_3$ with water, drying the paste and treating the cake as shown below. Particles sized $-250+150$ um were recovered from the calcined material.

| Example No. | Treatment | Hardness Index |
|---|---|---|
| 2 | None | 3 |
| 3 | Fired in $N_2$ at 1000° C. for 4 hours | 46 |
| 4 | Fired in $CO_2$ at 1000° C. for 4 hours | 64 |

The catalyst of example 4 was successfully used in a fluidised bed reactor.

EXAMPLES 5-7

A $SrCO_3$/bentonite catalyst was prepared by slurrying $SrCO_3$ together with 20% w/w bentonite, and drying the paste. The dried cake was crushed, pressed and particles sized −250+150 um recovered and given the following heat treatments.

| Example No | Treatment | Hardness Index |
|---|---|---|
| 5 | None | 15 |
| 6 | Fired in $N_2$ at 1000° C. for 4 hours | 60 |
| 7 | Fired in $CO_2$ at 1000° C. for 4 hours | 78 |

The catalyst of example 7 was successfully used in a fluidised-bed reactor.

EXAMPLES 8-13

A $SrCO_3$/$MgCO_3$ catalyst (nominally 15% w/w Sr) was prepared by precipitation from a solution of the corresponding nitrates with $(NH_4)_2CO_3$. The filter cake was slurried with a solution of the desired promotor, the paste dried and then pressed and particles sized −250+150 um recovered by crushing and sieving. Samples were subjected to the following heat treatments.

| Example No. | Treatment | Hardness Index |
|---|---|---|
| 8 | None | 31 |
| 9 | Heated in $N_2$ at 400° C. for 1 hour | 7 |
| 10 | Heated in $N_2$ at 1000° C. for 4 hours | 4 |
| 11 | heated in $N_2$ at 1200° C. for 4 hours | 13 |
| 12 | Heated in $CO_2$ at 1000° C. for 4 hours | 11 |
| 13 | Heated in $CO_2$ at 1200° C. for 4 hours | 69 |

The $MgCO_3$ component of this catalyst decomposed to MgO on heating at 400° C. resulting in a loss of hardness. The presence of MgO also necessitated a higher heat treatment temperature in $CO_2$ (Example 13) for the preparation of a catalyst suitable for use in a fluidised-bed reactor.

We claim:

1. A method for hardening particles of a catalyst containing a compound that is capable, under the hardening conditions, of existing at least partly in the form of a carbonate, comprising heating the catalyst particles to a temperature of at least 700° C. but below the melting point of the carbonate compound in an atmosphere containing carbon dioxide so as to retain that compound at least partly in the carbonate form for a period of time effective to sinter said catalyst particles.

2. A method as claimed in claim 1 in which the atmosphere contains carbon dioxide under a partial pressure above the dissociation pressure of the carbonate form of the catalyst compound.

3. A method as claimed in claim 1 in which the catalyst is heated to a temperature approaching, but below, the melting point of the carbonate compound.

4. A method as claimed in claim 1 in which the catalyst is heated for a period of at least one hour.

5. A method as claimed in claim 4 in which the catalyst is heated for a period of at least three hours.

6. A hardened catalyst produced by a method as claimed in any one of claims 1 to 5.

7. A hardened catalyst produced by a method for hardening particles of a catalyst containing a compound that is capable, under the hardening conditions, of existing at least partly in the form of a carbonate, comprising heating the catalyst particles to a temperature of at least 700° C. in an atmosphere containing carbon dioxide so as to retain that compound at least partly in the carbonate form for a period of time effective to sinter said catalyst particles wherein the catalyst contains a carbonate of a Group IIA element.

8. A hardened catalyst as claimed in claim 7 in which the catalyst contains strontium carbonate.

* * * * *